(12) United States Patent
Theodoridis et al.

(10) Patent No.: US 7,208,450 B2
(45) Date of Patent: Apr. 24, 2007

(54) PESTICIDAL (DIHALOPROPENYL) PHENYLALKYL SUBSTITUTED BENZOXAZOLE AND BENZOTHIAZOLE DERIVATIVES

(75) Inventors: George Theodoridis, Princeton, NJ (US); Edward J. Barron, Trenton, NJ (US); Dominic P. Suarez, Yardley, PA (US); Y. Larry Zhang, Kendall Park, NJ (US); Ping Ding, Lawrenceville, NJ (US); John W. Lyga, Basking Ridge, NJ (US); Matthew P. Whiteside, Morrisville, PA (US)

(73) Assignee: Bayer CropScience AG, Monheim (DE)

( * ) Notice: Subject to any disclaimer, the term of this patent is extended or adjusted under 35 U.S.C. 154(b) by 52 days.

(21) Appl. No.: 10/510,331

(22) PCT Filed: Apr. 28, 2004

(86) PCT No.: PCT/US2004/013014

§ 371 (c)(1),
(2), (4) Date: Oct. 5, 2004

(87) PCT Pub. No.: WO2004/099105

PCT Pub. Date: Nov. 18, 2004

(65) Prior Publication Data

US 2005/0171356 A1    Aug. 4, 2005

Related U.S. Application Data

(60) Provisional application No. 60/466,674, filed on Apr. 30, 2003.

(51) Int. Cl.
| | | |
|---|---|---|
| *A01N 43/76* | (2006.01) |
| *A01N 43/78* | (2006.01) |
| *C07D 263/54* | (2006.01) |
| *C07D 277/62* | (2006.01) |

(52) U.S. Cl. .................. 504/270; 504/267; 548/217; 548/152; 548/178

(58) Field of Classification Search ............. 548/152, 548/178, 217; 504/267, 270
See application file for complete search history.

(56) References Cited

U.S. PATENT DOCUMENTS

| 5,922,880 A | 7/1999 | Sakamoto et al. |
| 6,071,861 A | 6/2000 | Sakamoto et al. |
| 6,268,313 B1 | 7/2001 | Sakamoto et al. |
| 6,376,428 B1 | 4/2002 | Sakamoto et al. |
| 6,403,639 B1 | 6/2002 | Ishikawa et al. |
| 6,407,243 B1 | 6/2002 | Bryant et al. |
| 6,589,914 B2 | 7/2003 | Sakamoto et al. |

FOREIGN PATENT DOCUMENTS

WO    WO 2004/020445    3/2004

*Primary Examiner*—Joseph K. McKane
*Assistant Examiner*—Jason M. Nolan
(74) *Attorney, Agent, or Firm*—Sterne, Kessler, Goldstein & Fox, PLLC

(57) ABSTRACT

Certain novel (dihalopropenyl)phenylalkyl substituted benzoxazole and benzothiazole derivatives have unexpected insecticidal activity. These compounds are represented by formula (I): where R through $R^{11}$, inclusively. x, A, B, y, D, E and G are fully described herein. Preferred compounds of the present invention are those wherein the benzo-fused ring moiety is attached to the remainder of the molecule at the positions designated as (5) or (6) and where $R^{11}$ is either $C_1$–$C_3$ alkyl or halo $C_1$–$C_3$ alkyl. In addition, compositions comprising an insecticidally effective amount of at least one compound of formula (I), and optionally, an effective amount of at least one of a second compound, with at least one insecticidally compatible carrier are also disclosed; along with methods of controlling insects comprising applying said compositions to a locus where insects are present or are expected to be present.

13 Claims, No Drawings

PESTICIDAL (DIHALOPROPENYL) PHENYLALKYL SUBSTITUTED BENZOXAZOLE AND BENZOTHIAZOLE DERIVATIVES

This application claims the benefit of U.S. Provisional Application No. 60/466,674, filed Apr. 30, 2003.

FIELD OF THE INVENTION

The present invention relates to novel compounds and their use in controlling insects and acarids. In particular, it pertains to (dihalopropenyl)phenylalkyl substituted benzoxazole and benzothiazole derivatives and agriculturally acceptable salts thereof, compositions containing them and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Insecticides and acaricides are useful for controlling insects and acarids which may otherwise cause significant damage to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents and publications disclose a variety of dihalopropene compounds that are reported to be insecticidally and acaricidally active. For example, U.S. Pat. No. 5,922,880 discloses certain dihalopropene compounds containing optionally substituted heterocyclic ring groups for use as insecticides and acaricides. Examples of the heterocyclic ring in the optionally substituted heterocyclic ring group are isoxazole, thiazole, 1,3,4-thiadiazole, pyrrole, furan, thiophene, pyrazole, imidazole, 1,2,3-triazole, 1,2,4-triazole, 1,2,3,4-tetrazole, pyridine, pyridazine, pyrimdine, pyrazine, 1,2,4-triazine, 1,3,5-triazine, indole, benzofuran, thianaphthalene, indazole, benzimidazole, benzotriazole, benzisoxazole, benzoxazole, benzothiazole, quinoline, isoquinoline, quinoxaline, quinazole, piperidine, piperazine, tetrahydrofuran, tetrahydropyran, pyrazoline, phthalimide, dioxane, dioxolane, and benzodioxolane (Column 3, lines 15–25).

There is no disclosure or suggestion in the above-referenced patent of the structures and pesticidal activity of the compounds of the present invention.

SUMMARY OF THE INVENTION

In accordance with the present invention, it has now been found that certain novel (dihalopropenyl)phenylalkyl substituted benzoxazole and benzothiazole derivatives are surprisingly active in the control of insects and acarids when used in the insecticidal and acaricidal compositions and methods of this invention. The novel (dihalopropenyl)phenylalkyl substituted benzoxazole and benzothiazole derivatives are represented by the following general formula I:

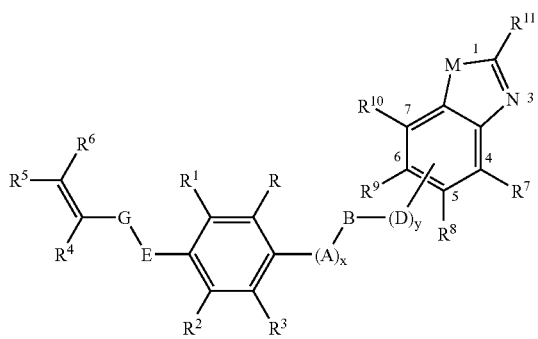

wherein
R and $R^3$ are independently selected from hydrogen, halogen, hydroxy, $(C_1–C_3)$alkyl, $(C_3–C_6)$cycloalkyl, $(C_2–C_5)$alkenyl, $(C_2–C_5)$alkynyl, halo$(C_1–C_3)$alkyl, $(C_1–C_3)$alkoxy, halo$(C_1–C_3)$alkoxy, $(C_1–C_3)$alkylthio, halo$(C_1–C_3)$alkylthio, $(C_1–C_3)$alkylsulfonyl, halo$(C_1–C_3)$alkylsulfonyl, cyano, nitro; optionally substituted amino wherein the optional substituent is selected from $(C_1–C_4)$alkyl, $(C_1–C_3)$alkylcarbonyl and $(C_1–C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(=J)—K, and —C($R^{12}$)—Q—$R^{13}$, wherein the optional substituent is selected from $(C_1–C_4)$alkyl, halo$(C_1–C_4)$alkyl, $(C_1–C_4)$alkoxy, $(C_1–C_4)$alkoxy$(C_1–C_4)$alkyl, $(C_3–C_6)$cycloalkyl, $(C_2–C_5)$alkenyl, $(C_2–C_5)$alkynyl, cyano, nitro and aryl;

where
J is selected from O, S, $NR^{14}$, and $NOR^{14}$, where $R^{14}$ is hydrogen, $(C_1–C_4)$alkyl, halo$(C_1–C_4)$alkyl, aryl and aryl$(C_1–C_4)$alkyl;
K is selected from hydrogen, $(C_1–C_3)$alkyl, halo$(C_1–C_3)$alkyl, $(C_1–C_3)$alkoxy, $(C_1–C_3)$alkylamino and di$(C_1–C_3)$alkylamino;
Q is selected from O, S, and $NR^{14}$, where $R^{14}$ is as previously described;
$R^{12}$ and $R^{13}$ are independently selected from hydrogen, $(C_1–C_4)$alkyl and halo$(C_1–C_4)$alkyl, and $R^{12}$ and $R^{13}$ may be taken together with -T(CH$R^{14})_m$—, where m is an integer of 2 to 4; T is selected from from O, S, and $NR^{14}$, where $R^{14}$ is as previously described;
$R^1$ and $R^2$ are independently selected from hydrogen, halogen and $(C_1–C_3)$alkyl;
$R^4$ is hydrogen;
$R^5$ and $R^6$ are independently selected from halogen;
E is selected from $CH_2$, O, S and $NR^{15}$ where $R^{15}$ is selected from hydrogen, $(C_1–C_3)$alkyl, $(C_1–C_3)$alkoxy$(C_1–C_3)$alkyl, aryl$(C_1–C_3)$alkyl, $(C_2–C_4)$alkenyl$(C_1–C_3)$alkyl, halo$(C_2–C_4)$alkenyl$(C_1–C_3)$alkyl, di$(C_1–C_3)$alkylphosphonate, formyl, $(C_1–C_3)$alkylcarbonyl, halo$(C_1–C_3)$alkylcarbonyl, $(C_1–C_3)$alkoxy$(C_1–C_3)$alkylcarbonyl, arylcarbonyl and $(C_1–C_3)$alkylsulfonyl;

G is selected from O, S, CH$_2$O* and (CH$_2$)$_n$ where the asterisk denotes attachment to E, and n is an integer selected from 1, 2 and 3, provided that E and G are not simultaneously O or S, x is an integer selected from 0 or 1;

and when x is 1,

A is selected from O, S(O)$_p$ and —NR$^{15}$, where p is an integer selected from 0, 1 and 2, and R$^{15}$ is as previously described;

B is a bridging group, *—(CR$^{16}$R$^{17}$)$_q$—(CR$^{18}$R$^{19}$)$_r$—(CR$^{20}$R$^{21}$)$_s$—L$_t$—(CR$^{22}$R$^{23}$)$_u$—(CR$^{24}$R$^{25}$)$_v$—(CR$^{26}$R$^{27}$)$_w$—, where the asterisk denotes attachment at A; q, r, s, u, v and w are integers independently selected from 0, 1 and 2;

and when q, r, s, u, v or w are 1 or 2,

R$^{16}$ through R$^{27}$, inclusively, are independently selected from hydrogen, (C$_1$–C$_3$)alkyl, halo(C$_1$–C$_3$)alkyl, (C$_1$–C$_3$)alkoxy(C$_1$–C$_3$)alkyl, and (C$_3$–C$_6$)cycloalkyl;

t is an integer selected from 0 or 1; and when t is 1,

L is selected from CH═CH; O, S(O)$_p$; OS(O)$_2$, S(O)$_2$O, NR$^{28}$; N(oxide)R$^{28}$; NR$^{28}$SO$_2$; NR$^{28}$C(═O)NR$^{29}$; Si(CH$_3$)$_2$; C(═O), OC(═O), NHC(═O); ON═CH; HC═NO; C(═O)O; C(═O)NH; C(═NOR$^{14}$) and [CR$^{30}$R$^{31}$]$_z$, where p is as previously described, R$^{28}$ and R$^{29}$ are independently selected from hydrogen, (C$_1$–C$_3$)alkyl, (C$_1$–C$_3$)alkylsulfonyl, (C$_1$–C$_3$)alkylcarbonyl, (C$_2$–C$_5$)alkenyl, and (C$_2$–C$_5$)alkynyl; z is an integer selected from 1 or 2; and R$^{30}$ and R$^{31}$ are independently selected from hydrogen and (C$_1$–C$_3$)alkyl;

y is an integer selected from 0 or 1;

and when y is 1,

D is selected from O; S(O)$_p$; and NR$^{15}$, where p and R$^{15}$ are as previously described, wherein D is attached to the benzo-fused ring moiety set forth in formula I at any one of the positions designated 4-, 5-, 6- or 7-:

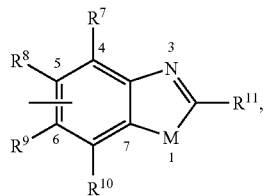

R$^7$, R$^8$, R$^9$ and R$^{10}$ are independently selected from hydrogen, halogen, (C$_1$–C$_4$)alkyl, (C$_3$–C$_6$)cycloalkyl, (C$_2$–C$_5$)alkenyl, (C$_2$–C$_5$)alkynyl, halo(C$_1$–C$_4$)alkyl, (C$_1$–C$_4$)alkoxy, halo(C$_1$–C$_4$)alkoxy, (C$_1$–C$_4$)alkylthio, halo(C$_1$–C$_4$)alkylthio, (C$_1$–C$_4$)alkylsulfonyl, halo(C$_1$–C$_4$)alkylsulfonyl, cyano, nitro, aryl, alkylcarbonylamino, arylcarbonylamino, and (C$_1$–C$_4$)alkoxycarbonylamino;

R$^{11}$ is selected from hydrogen, halogen, hydroxyl, cyano, (C$_1$–C$_6$)alkyl, (C$_1$–C$_6$)alkoxy, halo(C$_1$–C$_6$)alkyl, halo(C$_1$–C$_6$)alkoxy, (C$_2$–C$_6$)alkenyl, (C$_2$–C$_6$alkynyl, (C$_1$–C$_6$)cycloalkyl, amino, (C$_1$–C$_6$)alkylamino, di(C$_1$–C$_6$)alkylamino, (C$_1$–C$_6$)alkylthio, aryl, arylthio, tri(C$_1$–C$_6$)alkylsilyl, SF$_5$, C(═O)NR$^{14}$ and NOR$^{14}$ where R$^{14}$ is as previously described;

M is O or S;

and agriculturally acceptable salts thereof.

The present invention also includes compositions containing an insecticidally effective amount of at least one compound of formula I, and optionally, an effective amount of at least one second compound, with at least one insecticidally compatible carrier.

The present invention also includes methods of controlling insects, in an area where control is desired, which comprise applying an insecticidally effective amount of the above composition to the locus of crops, or other areas where insects are present or are expected to be present.

DETAILED DESCRIPTION OF THE INVENTION

The present invention relates to certain new and useful insecticidal and acaricidal compounds, namely (dihalopropenyl)phenylalkyl substituted benzoxazole and benzothiazole derivatives (hereinafter termed "compounds of formula I") as depicted in general formula I:

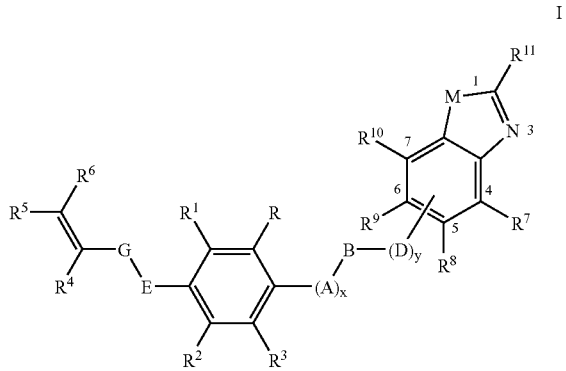

wherein

R and R$^3$ are independently selected from hydrogen, halogen, hydroxy, (C$_1$–C$_3$)alkyl, (C$_3$–C$_6$)cycloalkyl, (C$_2$–C$_5$)alkenyl, (C$_2$–C$_5$)alkynyl, halo(C$_1$–C$_3$)alkyl, (C$_1$–C$_3$)alkoxy, halo(C$_1$–C$_3$)alkoxy, (C$_1$–C$_3$)alkylthio, halo(C$_1$–C$_3$)alkylthio, (C$_1$–C$_3$)alkylsulfonyl, halo(C$_1$–C$_3$)alkylsulfonyl, cyano, nitro; optionally substituted amino wherein the optional substituent is selected from (C$_1$–C$_4$)alkyl, (C$_1$–C$_3$)alkylcarbonyl and (C$_1$–C$_3$)alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl, optionally substituted tetrahydrofuranyl, optionally substituted dioxolanyl, optionally substituted dioxanyl, —C(═J)—K, and —C(R$^{12}$)—Q—R$^{13}$, wherein the optional substituent is selected from (C$_1$–C$_4$)alkyl, halo(C$_1$–C$_4$)alkyl, (C$_1$–C$_4$)alkoxy, (C$_1$–C$_4$)alkoxy(C$_1$–C$_4$)alkyl, (C$_3$–C$_6$)cycloalkyl, (C$_2$–C$_5$)alkenyl, (C$_2$–C$_5$)alkynyl, cyano, nitro and aryl;

where

J is selected from O, S, NR$^{14}$, and NOR$^{14}$, where R$^{14}$ is hydrogen, (C$_1$–C$_4$)alkyl, halo(C$_1$–C$_4$)alkyl, aryl and aryl(C$_1$–C$_4$)alkyl;

K is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;

Q is selected from O, S, and $NR^{14}$, where $R^{14}$ is as previously described;

$R^{12}$ and $R^{13}$ are independently selected from hydrogen, $(C_1-C_4)$alkyl and halo$(C_1-C_4)$alkyl, and $R^{12}$ and $R^{13}$ may be taken together with $-T(CHR^{14})_m-$, where m is an integer of 2 to 4; T is selected from from O, S, and $NR^{14}$, where $R^{14}$ is as previously described;

$R^1$ and $R^2$ are independently selected from hydrogen, halogen and $(C_1-C_3)$alkyl;

$R^4$ is hydrogen;

$R^5$ and $R^6$ are independently selected from halogen;

E is selected from $CH_2$, O, S and $NR^{15}$ where $R^{15}$ is selected from hydrogen, $(C_1-C_3)$alkyl, $(C_1-C_3)$alkoxy$(C_1-C_3)$alkyl, aryl$(C_1-C_3)$alkyl, $(C_2-C_4)$alkenyl$(C_1-C_3)$alkyl, halo$(C_2-C_4)$alkenyl$(C_1-C_3)$alkyl, di$(C_1-C_3)$alkylphosphonate, formyl, $(C_1-C_3)$alkylcarbonyl, halo$(C_1-C_3)$alkylcarbonyl, $(C_1-C_3)$alkoxy$(C_1-C_3)$alkylcarbonyl, arylcarbonyl and $(C_1-C_3)$alkylsulfonyl;

G is selected from O, S, $CH_2O^*$ and $(CH_2)_n$ where the asterisk denotes attachment to E, and n is an integer selected from 1, 2 and 3, provided that E and G are not simultaneously O or S, x is an integer selected from 0 or 1;

and when x is 1,

A is selected from O, $S(O)_p$ and $-NR^{15}$, where p is an integer selected from 0, 1 and 2, and $R^{15}$ is as previously described;

B is a bridging group, $*-(CR^{16}R^{17})_q-(CR^{18}R^{19})_r-(CR^{20}R^{21})_s-L_t-(CR^{22}R^{23})_u-(CR^{24}R^{25})_v-(CR^{26}R^{27})_w-$, where the asterisk denotes attachment at A; q, r, s, u, v and w are integers independently selected from 0, 1 and 2;

and when q, r, s, u, v or w are 1 or 2, $R^{16}$ through $R^{27}$, inclusively, are independently selected from hydrogen, $(C_1-C_3)$alkyl, halo$(C_1-C_3)$alkyl, $(C_1-C_3)$alkoxy$(C_1-C_3)$alkyl, and $(C_3-C_6)$cycloalkyl;

t is an integer selected from 0 or 1; and when t is 1,

L is selected from $CH=CH$; O, $S(O)_p$; $OS(O)_2$, $S(O)_2O$, $NR^{28}$; $N(oxide)R^{28}$; $NR^{28}SO_2$; $NR^{28}C(=O)NR^{29}$; $Si(CH_3)_2$; $C(=O)$, $OC(=O)$, $NHC(=O)$; $ON=CH$; $HC=NO$; $C(=O)O$; $C(=O)NH$; $C(=NOR^{14})$ and $[CR^{30}R^{31}]_z$, where p is as previously described, $R^{28}$ and $R^{29}$ are independently selected from hydrogen, $(C_1-C_3)$alkyl, $(C_1-C_3)$alkylsulfonyl, $(C_1-C_3)$alkylcarbonyl, $(C_2-C_5)$alkenyl, and $(C_2-C_5)$alkynyl; z is an integer selected from 1 or 2; and $R^{30}$ and $R^{31}$ are independently selected from hydrogen and $(C_1-C_3)$alkyl;

y is an integer selected from 0 or 1;

and when y is 1,

D is selected from O; $S(O)_p$; and $NR^{15}$, where p and $R^{15}$ are as previously described, wherein D is attached to the benzo-fused ring moiety set forth in formula I at any one of the positions designated 4-, 5-, 6- or 7-:

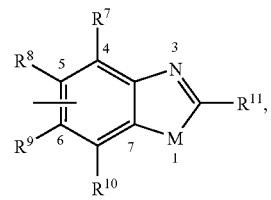

$R^7$, $R^8$, $R^9$ and $R^{10}$ are independently selected from hydrogen, halogen, $(C_1-C_4)$alkyl, $(C_3-C_6)$cycloalkyl, $(C_2-C_5)$alkenyl, $(C_2-C_5)$alkynyl, halo$(C_1-C_4)$alkyl, $(C_1-C_4)$alkoxy, halo$(C_1-C_4)$alkoxy, $(C_1-C_4)$alkylthio, halo$(C_1-C_4)$alkylthio, $(C_1-C_4)$alkylsulfonyl, halo$(C_1-C_4)$alkylsulfonyl, cyano, nitro, aryl, alkylcarbonylamino, arylcarbonylamino, and $(C_1-C_4)$alkoxycarbonylamino;

$R^{11}$ is selected from hydrogen, halogen, hydroxyl, cyano, $(C_1-C_6)$alkyl, $(C_1-C_6)$alkoxy, halo$(C_1-C_6)$alkyl, halo$(C_1-C_6)$alkoxy, $(C_2-C_6)$alkenyl, $(C_2-C_6)$alkynyl, $(C_1-C_6)$cycloalkyl, amino, $(C_1-C_6)$alkylamino, di$(C_1-C_6)$alkylamino, $(C_1-C_6)$alkylthio, aryl, arylthio, tri$(C_1-C_6)$alkylsilyl, $SF_5$, $C(=O)NR^{14}$ and $NOR^{14}$ where $R^{14}$ is as previously described;

M is O or S;

and agriculturally acceptable salts thereof.

Preferred (dihalopropenyl)phenylalkyl substituted benzoxazole and benzothiazole derivatives from the group set forth above are those where R and $R^3$ are independently selected from halogen and $(C_1-C_3)$alkyl;

$R^1$, $R^2$, and $R^4$ are hydrogen;

$R^5$ and $R^6$ are independently selected from chlorine, bromine, and fluorine;

E is O;

G is $(CH_2)_n$, where n is 1;

x is 1, and A is O;

and when q, r, s, u, v and w are 1 or 2, $R^{16}$ through $R^{27}$ inclusively, are hydrogen;

t is 0 or 1, and when t is 1,

L is selected from O, $OC(=O)$, $NHC(=O)$, $ON=CH$, and $CH=NO$;

y is 1, and

D is selected from O; $S(O)_p$; and $NR^{15}$, where p is 0, and $R^{15}$ is selected from hydrogen, $(C_1-C_3)$alkyl, aryl$(C_1-C_3)$alkyl, $(C_2-C_4)$alkenyl$(C_1-C_3)$alkyl, and halo$(C_2-C_4)$alkenyl$(C_1-C_3)$alkyl;

$R^7$, $R^8$, $R^9$ and $R^{10}$ are independently selected from hydrogen, halogen, halo$(C_1-C_4)$alkyl and nitro;

and $R^{11}$ is selected from $(C_1-C_4)$alkyl and halo$(C_1-C_4)$alkyl;

More preferred (dihalopropenyl)phenylalkyl substituted benzoxazole and benzothiazole derivatives from the group set forth above are those where R and $R^3$ are independently selected from chlorine and methyl; $R^5$ and $R^6$ are independently selected from chlorine and bromine; q, r, s, u, v and w are 1 or 2, provided that the sum of q, r, s, u, v and w is at least 2 and at most 6; t is 0; D is O, wherein D is attached to the benzo-fused moiety set forth in formula I at the position designated as 5 or 6; $R^7$, $R^8$, $R^9$ and $R^{10}$ are hydrogen; and $R^{11}$ is methyl or trifluoromethyl. Yet more preferred are those where i) R, $R^3$, $R^5$ and $R^6$ are each chlorine; q, r and s are 1; u and v are 0 or 1; w is 0; M is O and $R^{11}$ is trifluoromethyl; and ii) R, $R^3$, $R^5$ and $R^6$ are each chlorine; q, r and s are 1; u and v are 0 or 1; w is 0; M is S and $R^{11}$ is methyl.

More specifically, the new and useful insecticidal and acaricidal (dihalopropenyl)phenylalkyl substituted benzoxazole and benzothiazole derivatives of formula I are as shown below:

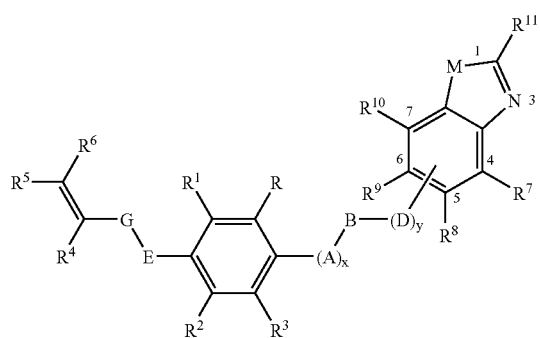

I wherein

R and $R^3$ are independently selected from hydrogen, halogen or $(C_1-C_3)$alkyl;

$R^1$ and $R^2$ are hydrogen;

E is O; G is $(CH_2)_n$ where n is 1;

$R^4$ is hydrogen;

$R^5$ and $R^6$ are independently selected from halogen;

x is 1 and A is O;

B is a bridging group *—$(CR^{16}R^{17})_q$—$(CR^{18}R^{19})_r$—$(CR^{20}R^{21})_s$—$L_t$—$(CR^{22}R^{23})_u$—$(CR^{24}R^{25})_v$—$(CR^{26}R^{27})_w$—, where the asterisk denotes attachment at A; q, r, s, u, v and w are integers independently selected from 0, 1 and 2; and t is 0;

and when q, r, s, u, v or w are 1 or 2, $R^{16}$ through $R^{27}$, inclusively, are hydrogen, y is 1, and D is O, and wherein D is attached to the benzo-fused ring moiety set forth in formula I at either one of the positions designated 5- or 6-:

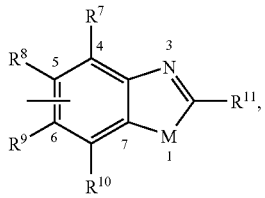

$R^7$, $R^8$, $R^9$ and $R^{10}$ are independently selected from hydrogen, halogen or $(C_1-C_4)$alkyl; and $R^{11}$ is selected from $(C_1-C_3)$alkyl and halo$(C_1-C_3)$alkyl.

Preferred of the more specific (dihalopropenyl)phenylalkyl substituted benzoxazole and benzothiazole derivatives are those where R and $R^3$ are independently selected from chlorine and methyl; $R^5$ and $R^6$ are independently selected from chlorine and bromine; q, r, s, u, v and w are 1 or 2, provided that the sum of q, r, s, u, v and w is at least 2 and at most 6; $R^7$, $R^8$, $R^9$ and $R^{10}$ are hydrogen; and $R^{11}$ is methyl or trifluoromethyl. Yet more preferred are those where i) R, $R^3$, $R^5$ and $R^6$ are each chlorine; q, r and s are 1; u and v are 0 or 1; w is 0; M is O and $R^{11}$ is trifluoromethyl; and ii) where R, $R^3$, $R^5$ and $R^6$ are each chlorine; q, r and s are 1; u and v are 0 or 1; w is 0; M is S and $R^{11}$ is methyl.

The most preferred compounds are those in which (a) the linker group $(A)_x$—B—$(D)_y$— is $O(CH2)_nO$— where n is equal to from 2 to 6 (b) the linker group is attached to the benzo ring of the benzoxazole or benzothiazole at either position 5 or 6 on that ring and (c) $R^{11}$ is CH3 or CF3. Of these especially preferred compounds are those where (a) M is O (b) the linker is attached at the 6 position (c) n is 3 to 5 and (d) $R^{11}$ is $CF_3$.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention comprise causing an insecticidally effective amount of a compound of formula I to be administered to insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which are referred to as pro-insecticides.

Another aspect of the present invention relates to compositions containing an insecticidally effective amount of at least one compound of formula I.

Another aspect of the present invention relates to compositions containing an insecticidally effective amount of at least one compound of formula I, and an effective amount of at least one second compound.

Another aspect of the present invention relates to methods of controlling insects by applying an insecticidally effective amount of a composition as set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp, *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having six to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of; while the term "TLC analysis" refers to thin layer chromatographic analysis of, for example a reaction mixture. The term "HPLC" refers to high pressure liquid chromatography, as it relates to, for example a method of separating components from a reaction mixture. The term "DMF" refers to N,N-dimethylformamide. The term "THF" refers to tetrahydrofuran. The term "DBU" refers to 1,8-diazabicyclo[5.4.0]undec-7-ene. The term "DEAD" refers to diethyl azodicarboxylate. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids. The term "independently selected from" as set forth above and in the claims section of the present specification refers to the possibility that moieties, for example the $R^5$ and $R^6$, may be the same or they may be different within the group that the selection is made.

The (dihalopropenyl)phenylalkyl substituted benzoxazole and benzothiazole derivatives of formula I can be synthesized by methods that are individually known to one skilled in the art from available intermediate compounds.

Scheme 1 below illustrates a general procedure for synthesizing compounds of formula I where, for example, $R^1$, $R^2$, $R^4$, $R^7$, $R^8$, $R^9$ and $R^{10}$ are hydrogen; R, $R^3$, $R^5$ and $R^6$ are chlorine; E is O; G is $(CH_2)_n$ where n is 1; x and y are 1, and A and D are O; B is the bridging group as set forth above where q, r, s and u are 1, and t, v and w are 0; M is O and $R^{11}$ is $CF_3$:

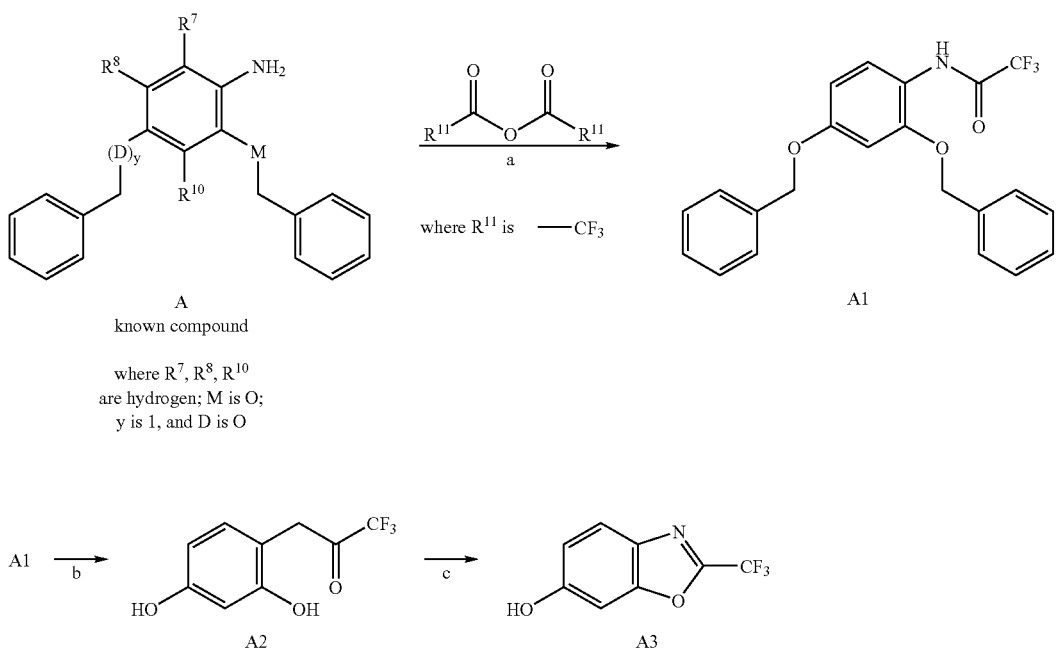

-continued

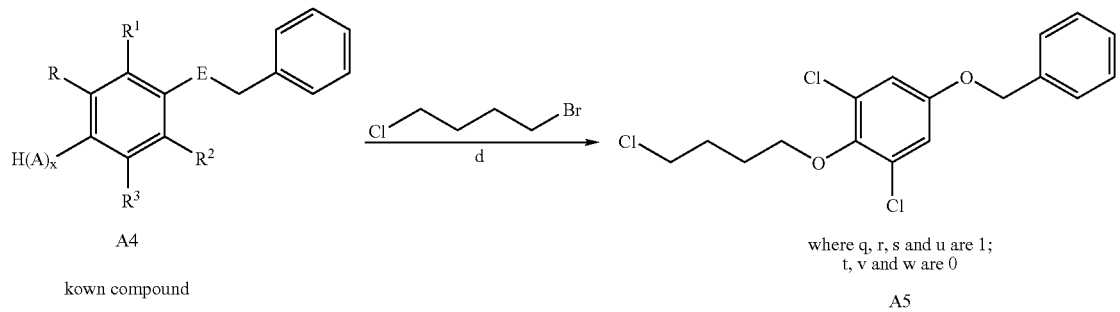

A4
kown compound where R and R³ are chlorine;
R¹ and R²are hydrogen; x is
1 and A is O; E is O where q, r, s and u are 1;
t, v and w are 0
A5

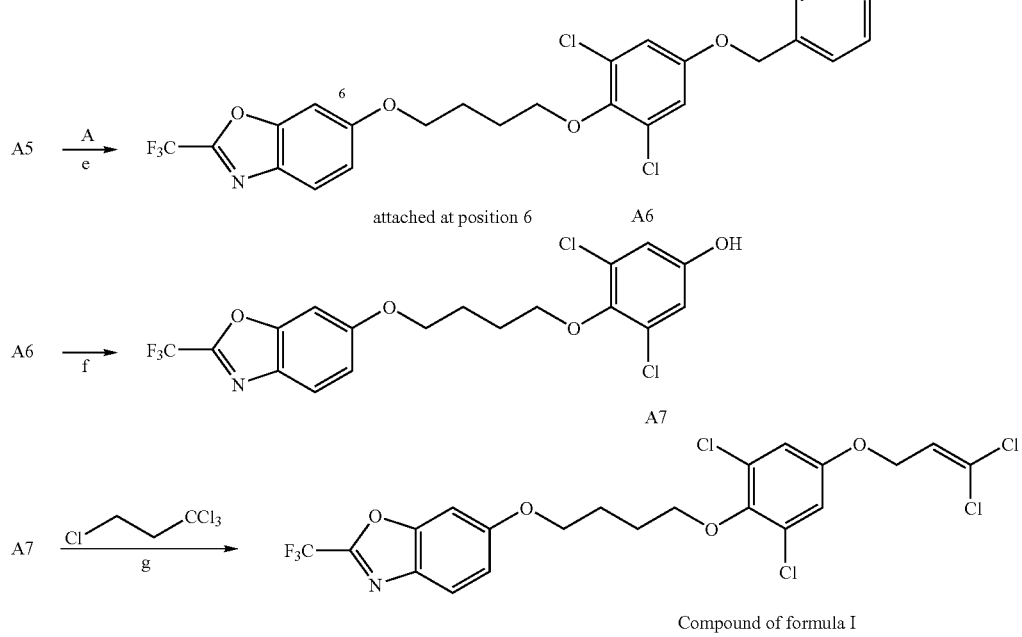

Compound of formula I where E is O; G is CH₂;
R⁴ is hdrogen, and R⁵ and
R⁶ are chlorine a) Et₃N/THF/RT-reflux b) H₂(g)/10% Pd on carbon/ EtOH c) p-toluenesulfonic acid/Toluene
d) K₂CO₃/DMF/0° C.-RT e) K₂CO₃/DMF/80° C. f) H₂(g)/10% Pd on carbon/EtOH g) K₂CO₃/DMF/80° C.

As depicted in Scheme 1 the known compound, for example 2,4-bis(phenylmethoxy)phenylamine (A), was reacted with an appropriate anhydride such as trifluoroacetic anhydride, yielding the corresponding bis(phenylmethoxy)phenyl]-2,2,2-trifluoroacetamide (A1). Intermediate (A1) was in turn deprotected with hydrogen gas under catalytic conditions, affording the corresponding (2,4-dihydroxyphenyl)-2,2,2-trifluoroacetamide (A2). Intermediate (A2) was then cyclized by dehydration, providing the corresponding intermediate 2-(trifluoromethyl)benzoxazol-6-ol (A3).

To prepare a second intermediate the known compound, for example 2,6-dichloro-4-phenylmethoxyphenol (A4), was reacted with a haloalkane of appropriate chain length, such as 1-bromo-4-chlorobutane, affording the corresponding haloalkoxybenzene derivative (A5). The benzoxazol-6-ol, intermediate (A3) above, was then reacted under basic conditions with intermediate (A5), yielding the corresponding substituted benzoxazole (A6). Intermediate (A6) was then deprotected as set forth above, yielding the phenolic intermediate (A7); which was in turn reacted with an appropriate haloalkane under basic conditions, providing a compound of formula I, as described above. Example 1, set forth below describes in detail how compounds of formula I shown in Scheme 1 were prepared.

Scheme 2 below illustrates a general procedure for synthesizing compounds of formula I where, for example, R¹, R², R⁴, R⁷, R⁸, R⁹ and R¹⁰ are hydrogen; R, R³, R⁵ and R⁶ are chlorine; E is O; G is (CH₂)$_n$ where n is 1; x and y are 1, and A and D are O; B is the bridging group as set forth above where q, r, and s are 1, and t, u, v and w are 0; M is O and R¹¹ is —CH₃:

Scheme 2

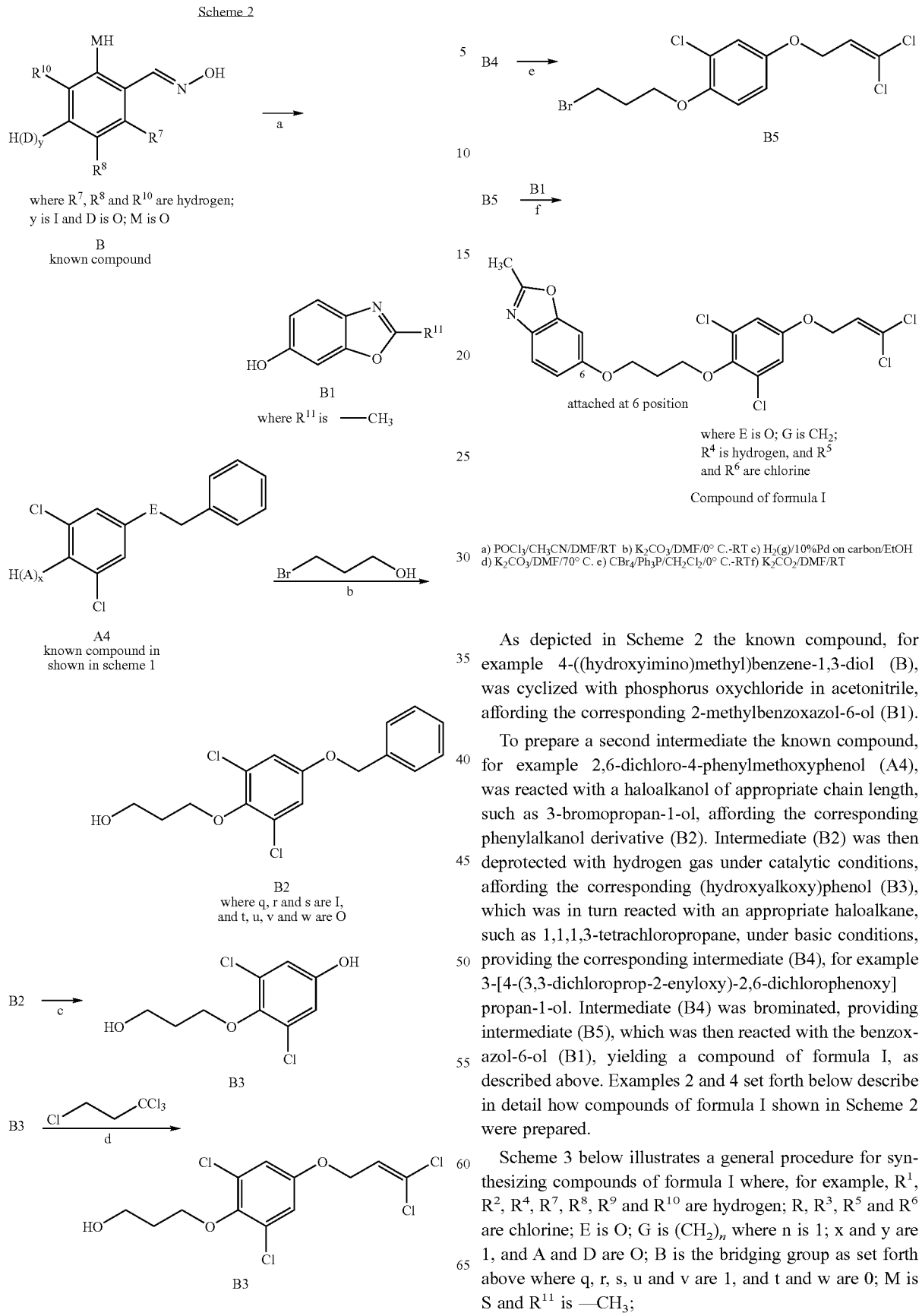

a) POCl₃/CH₃CN/DMF/RT  b) K₂CO₃/DMF/0° C.-RT c) H₂(g)/10%Pd on carbon/EtOH
d) K₂CO₃/DMF/70° C. e) CBr₄/Ph₃P/CH₂Cl₂/0° C.-RTf) K₂CO₂/DMF/RT As depicted in Scheme 2 the known compound, for example 4-((hydroxyimino)methyl)benzene-1,3-diol (B), was cyclized with phosphorus oxychloride in acetonitrile, affording the corresponding 2-methylbenzoxazol-6-ol (B1).

To prepare a second intermediate the known compound, for example 2,6-dichloro-4-phenylmethoxyphenol (A4), was reacted with a haloalkanol of appropriate chain length, such as 3-bromopropan-1-ol, affording the corresponding phenylalkanol derivative (B2). Intermediate (B2) was then deprotected with hydrogen gas under catalytic conditions, affording the corresponding (hydroxyalkoxy)phenol (B3), which was in turn reacted with an appropriate haloalkane, such as 1,1,1,3-tetrachloropropane, under basic conditions, providing the corresponding intermediate (B4), for example 3-[4-(3,3-dichloroprop-2-enyloxy)-2,6-dichlorophenoxy] propan-1-ol. Intermediate (B4) was brominated, providing intermediate (B5), which was then reacted with the benzoxazol-6-ol (B1), yielding a compound of formula I, as described above. Examples 2 and 4 set forth below describe in detail how compounds of formula I shown in Scheme 2 were prepared.

Scheme 3 below illustrates a general procedure for synthesizing compounds of formula I where, for example, $R^1$, $R^2$, $R^4$, $R^7$, $R^8$, $R^9$ and $R^{10}$ are hydrogen; R, $R^3$, $R^5$ and $R^6$ are chlorine; E is O; G is $(CH_2)_n$ where n is 1; x and y are 1, and A and D are O; B is the bridging group as set forth above where q, r, s, u and v are 1, and t and w are 0; M is S and $R^{11}$ is —$CH_3$;

Scheme 3

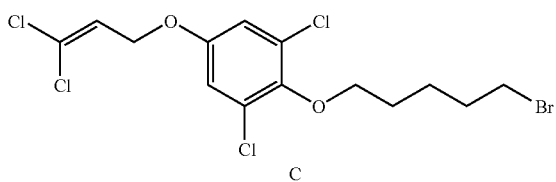

where q, r, s, u and v are 1
Prepared as in the preparation
of B2 through B5 of Scheme 2

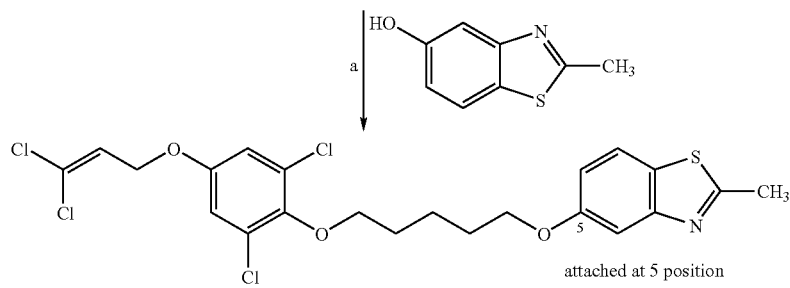

Compound of formula I a) $K_2CO_3$/DMF/RT

As depicted in Scheme 3, a 5-bromopentyloxy-1,3-dichlorobenzene (C) was prepared in a manner set forth for intermediates (B2) through (B5) in Scheme 2. Intermediate (C) was then reacted with an appropriate hydroxy compound, for example the known compound 2-methyl-5-benzothiazolol, providing a compound of formula I. Example 3, set forth below describes in detail how compounds of formula I shown in Scheme 3 were prepared.

One skilled in the art will, of course, recognize that the formulation and mode of application of a toxicant may affect the activity of the material in a given application. Thus, for agricultural use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carries for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifile concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxlic acid ("imazapyr"), a reaction product comprising (+/−)-2-[4,5-dihydro-4-methyl-4-(1-methylethyl)-5-oxo-1H-imidazol-2-yl]-4-methyl-binzoic acid and (+/−)2-[4,5-dihydro-4-methyl-4-(1-methylethyl)-5-oxo-1H-imidazol-2-yl]-5methylbenzoic acid ("imazamethabenz"), (+/−)-2-[4,5-dihydro-4-methyl-4-(1-methylethyl)-5-oxo-1H-imidazol-2-yl]-5-ethyl-3-pyridincarboxylic acid ("imazethapyr"), and (+/−)-2-[4,5-dihydro-4-methyl-4-(1-methylethyl)-5-oxo-1H-imidazol-2-yl]-3quinolinecarboxylic acid ("imazaquin"); duogebtk ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl -1,3,5-triazin-2-yl)amino]carbonyl]benzenesulfonamide (achlorsulfuron"), 2-([[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benczenesulfonamide ("triasulfuron"); 2-(4-aryloxy-phenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy]propanoic acid ("fluazifop"), (+/−)-2-[4-(6chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichoro-6-fluoro-2-pyridinyl)oxy]acetic acid ("fluroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, bifenthrin, cypermethrin, resolved cyhalothrin, etofenprox, esfenvalerate, tralomehtrin, tefluthrin, cycloprothrin, beta-cyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procynudone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldicarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium,* and soil-borne *cyanobacteria.*

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates one protocol for the preparation of 5-(3,3-dichloroprop-2-enyloxy)-1,3-dichloro-2-{4-[2-(trifluoromethyl)benzoxazol-6-yloxy]butoxy}benzene (Compound 6 in table below)

Step A Synthesis of N-[2,4-bis(phenylmethoxy)phenyl]-2,2,2-trifluoroacetamide as an Intermediate A solution of 1.7 grams (0.0055 mole) of 2,4-bis(phenylmethoxy)phenylamine (known compound) in 50 mL of THF was stirred and 0.8 mL (0.0055 mole) of trifluoroacetic anhydride was added. Upon completion of addition, 0.92 mL (0.0066 mole) of triethylamine was added dropwise during a one-hour period. Upon completion of addition the reaction mixture was warmed to reflux where it stirred for three hours. After this time the reaction mixture was cooled and concentrated under reduced pressure to a residue. The residue was taken up in 50 mL of water and extracted with three 50 mL portions of diethyl ether. The combined extracts were dried with sodium sulfate, filtered, and concentrated under reduced pressure to a residue. The residue was purified with column chromatography on silica gel using 1:1 methylene chloride:hexane as an eluant. The appropriate fractions were combined and concentrated under reduced pressure, yielding 1.7 grams of the subject compound. The NMR spectrum was consistent with the proposed structure.

Step B Synthesis of N-(2,4-dihydroxyphenyl)-2,2,2-trifluoroacetamide as an Intermediate A mixture of 1.5 grams (0.0036 mole) of, N-[2,4-bis(phenylmethoxy)phenyl]-2,2,2-trifluoroacetamide and 0.2 gram (catalyst) of 10% palladium on carbon in 125 mL of ethanol was treated with hydrogen gas in a Parr Hydrogenator, yielding 0.80 gram of the subject compound. The NMR spectrum was consistent with the proposed structure.

Step C Synthesis of 2-(trifluoromethyl)benzoxazol-6-ol as an Intermediate

A stirred solution of 0.8 gram (0.0036) of N-(2,4-dihydroxyphenyl)-2,2,2-trifluoroacetamide and a catalytic amount of p-toluenesulfonic acid in 50 mL of toluene was heated at reflux during an 18 hour period while the theoretical amount of water by-product was collected in a Dean-Stark trap. After this time the reaction mixture was concentrated under reduced pressure to a residue. The residue was purified with column chromatography on silica gel using methylene chloride as an eluant. The appropriate fractions were combined and concentrated under reduced pressure, yielding 0.3 gram of the subject compound. The NMR spectrum was consistent with the proposed structure.

Step D Synthesis of 1,3-dichloro-2-(4-chlorobutoxy)-5-(phenylmethoxy)benzene as an Intermediate A stirred solution of 10.0 grams (0.037 mole) of 2,6-dichloro-4-phenylmethoxyphenol (known compound) and 4.7 grams (0.041 mole) of 1-bromo-4-chlorobutane in 225 mL of DMF was cooled in an ice bath, and 7.7 grams (0.060 mole) of potassium carbonate was added. Upon completion of addition, the reaction mixture was allowed to warm to ambient temperature as it stirred for about 18 hours. The reaction mixture was then poured into 1000 mL of an aqueous solution saturated with sodium chloride. The mixture was extracted with four 150 mL portions of diethyl ether, and the combined extracts were washed with 50 mL of water. The organic layer was dried with sodium sulfate, filtered, and concentrated under reduced pressure to a residue. The residue was purified with column chromatography on silica gel using 1:3 methylene chloride:hexane as an eluant. The appropriate fractions were combined and concentrated under reduced pressure, yielding 10.7 grams of the subject compound. The NMR spectrum was consistent with the proposed structure.

Step E Synthesis of 1,3-dichloro-5-(phenylmethoxy)-2-{4-(trifluoromethyl)benzoxazol-6-yloxy]butoxy}benzene as an as an Intermediate A stirred solution of 0.5 gram (0.0014 mole) of 1,3-dichloro-2-(4-chlorobutoxy)-5-(phenylmethoxy)benzene, 0.3 gram (0.0014 mole) of 2-(trifluoromethyl)benzoxazol-6-ol and 0.39 gram (0.0028 mole) of potassium carbonate in 50 mL of DMF was heated to 80° C. where it stirred during an 18 hour period. After this time the reaction mixture was cooled, and 150 mL of water was added. The mixture was then saturated with solid sodium chloride and extracted with three 75 mL portions of diethyl ether. The combined extracts were washed with one 75 mL portion of water. The organic layer was dried with sodium sulfate, filtered, and the filtrate was concentrated under reduced pressure to a residue. The residue was purified with column chromatography on silica gel using 1:3 methylene chloride:hexane as an eluant. The appropriate fractions were combined and concentrated under reduced pressure, yielding 0.22 gram of the subject compound. The NMR spectrum was consistent with the proposed structure.

Step F Synthesis of 3,5-dichloro-4-{4-[2-(trifluoromethyl)benzoxazol-6-yloxy]butoxy}phenol as an Intermediate This compound was prepared in a manner analogous to that set forth in Step B of the present Example; by the treatment of 0.2 gram (0.00038 mole) of 1,3-dichloro-5-(phenylmethoxy)-2-{4-(trifluoromethyl)benzoxazol-6-yloxy]butoxy}benzene with hydrogen gas in the presence of 0.05 gram (catalyst) of 10% palladium on carbon in 50 mL of ethanol using a Parr hydrogenation apparatus. The yield of the subject compound was 0.15 gram.

Step G Synthesis of Compound 6

This compound was prepared in a manner analogous to that set forth in Step D of the present Example; by the reaction of 0.15 gram (0.00034 mole) of 3,5-dichloro-4-{4-[2-(trifluoromethyl)benzoxazol-6-yloxy]butoxyl}phenol, 0.1 gram (0.00052 mole) of 1,1,1,3-tetrachloropropane, and 0.1 gram (0.00072 mole) of potassium carbonate in 8 mL of DMF. The reaction product was purified with column chromatography on silica gel using 1:3 and 1:1 mixtures of methylene chloride:hexane as eluants. The appropriate fractions were combined and concentrated under reduced pressure, yielding 0.06 gram of Compound 6. The NMR spectrum was consistent with the proposed structure.

EXAMPLE 2

This example illustrates one protocol for the preparation of 5-(3,3-dichloroprop-2-enyloxy)-1,3-dichloro-2-[3-(methylbenzoxazol-6-yloxy)propoxyl]benzene (Compound 2 in table below)

Step A Synthesis of 4-((hydroxyimino)methyl)benzene-1,3-diol as an Intermediate A stirred solution of 2.0 grams (0.013 mole) of 1-(2,4-dihydroxyphenyl)ethan-1-one (commercially available) and 1.4 grams (0.019 mole) of hydroxylamine hydrochloride in 20 mL of water and 100 mL of ethanol was cooled to about 0° C. to 4° C. and 2.7 grams (0.068 mole) of sodium hydroxide was added. Upon completion of addition the reaction mixture was warmed to reflux where it stirred during a 30 minute period. After this time the reaction mixture was cooled to ambient temperature and 400 mL of aqueous 5% hydrochloric acid was added. The mixture was extracted with diethyl ether, and the extract was washed with water. The organic layer was dried with sodium sulfate, filtered, and the filtrate was concentrated under reduced pressure, yielding 1.5 grains of the subject compound.

Step B Synthesis of 2-methylbenzoxazol-6-ol as an Intermediate

A solution of 1.5 grams (0.009 mole) of 4-((hydroxyimino)methyl)benzene-1,3-diol in 5 mL of DMF and 15 mL of acetonitrile was stirred and 1.3 mL (0.014 mole) of phosphorus oxychloride was added portionwise. Upon completion of addition the reaction mixture was stirred for an additional one hour. After this time the reaction mixture was stirred with ice and water that contained 3.0 grams of sodium acetate, and extracted with diethyl ether. The extract was washed with water, dried with sodium sulfate and filtered. The filtrate was concentrated under reduced pressure to a residue. The residue was purified with column chromatography on silica gel using mixtures of ethyl acetate and hexane, and finally 100% ethyl acetate, as eluants. The appropriate fractions were combined and concentrated under reduced pressure, yielding 0.75 gram of the subject compound. The NMR spectrum was consistent with the proposed structure.

Step C Synthesis of 3-[2,6-dichloro-4-(phenylmethoxy)phenoxy]propan-1-ol as an Intermediate A stirred solution of 10.1 grams (0.038 mole) of 2,6-dichloro-4-(phenylmethoxy)phenol (known compound) and 8.0 grams (0.058 mole) of potassium carbonate in 150 mL of DMF was cooled to 0–4° C. and 3.7 mL (0.041 mole) of 3-bromopropan-1-ol was slowly added. Upon completion of addition the reaction mixture was allowed to warm to ambient temperature where it was stirred during an 18 hour period. After this time water was added to the reaction mixture, and the mixture was extracted with two 150 mL portions of diethyl ether. The combined extracts were dried with sodium sulfate, filtered, and the filtrate was concentrated under reduced pressure to yield 11.8 grams of residual solid. The NMR spectrum was consistent with the proposed structure.

Step D Synthesis of 3,5-dichloro-4-(3-hydroxypropoxy)phenol as an intermediate

This compound was prepared in a manner analogous to that of Step B of Example 1, by the treatment of 11.8 grams (0.036 mole) of 3-[2,6-dichloro-4-(phenylmethoxy)phenoxy]propan-1-ol with hydrogen gas in the presence of a catalytic amount of 10% palladium on carbon in ethanol using a Parr hydrogenation apparatus. Following the theoretical uptake of hydrogen, the reaction mixture was and filtered and concentrated under reduced pressure to a residue, yielding 8.0 grams of the subject compound.

Step E Synthesis of 3-[4-(3,3-dichloroprop-2-enyloxy)-2,6-dichlorophenoxy]propan-1-ol as an intermediate This compound was prepared in a manner analogous to that of Step D of Example 1, by the reaction of 8.0 grams (0.034 mole) of 3,5dichloro-4-(2-hydroxypropoxy)phenol, 10.1 grams (0.056 mole) of 1,1,1,3-tetrachloropropane and 10.8 grams (0.078 mole) of potassium carbonate in 100 mL of DMF. The reaction product was purified with column chromatography on silica gel using 1:2 methylene chloride: hexane as an eluant. The appropriate fractions were combined and concentrated under reduced pressure, yielding 9.1 grams of the subject compound. The NMR spectrum was consistent with the proposed structure.

Step F Synthesis of 1-[4-(3,3-dichloroprop-2-enyloxy)-2,6-dichlorophenoxy]-3-bromopropane as an intermediate A stirred solution of 3.5 grams (0.010 mole) of 3-[4-(3,3-dichloroprop-2-enyloxy)-2,6-dichlorophenoxy]propan-1-ol and 3.3 grams (0.010 mole) of carbon tetrabromide in 50 mL of methylene chloride was cooled to 0–4° C. and 2.9 grams (0.011 mole) of triphenylphosphine was added portion-wise. Upon completion of addition the reaction mixture was allowed to warm to ambient temperature where it stirred during a 42 hour period. After this time the reaction mixture was concentrated under reduced pressure to a residue. The residue was purified with column chromatography on silica gel using 1:3 methylene chloride:hexane as an eluant. The appropriate fractions were combined and concentrated under reduced pressure, yielding 7.7 grams of the subject compound. The NMR spectrum was consistent with the proposed structure.

Step G Synthesis of Compound 2

This compound was prepared in a manner analogous to that of Step D of Example 1, by the reaction of 0.27 gram (0.00067 mole) of 1-[4-(3,3-dichloroprop-2-enyloxy)-2,6-dichlorophenoxy]-3-bromopropane, 0.1 gram (0.00067 mole) of 2-methylbenzoxazol-6-ol (prepared in Step B of the present Example) and 0.37 gram (0.0027 mole) of potassium carbonate in 2 mL of DMF. The reaction product was purified with column chromatography on silica gel using 5% methylene chloride in hexane, and finally 100% methylene chloride, as eluants. The appropriate fractions were combined and concentrated under reduced pressure, yielding Compound 2.

EXAMPLE 3

This example illustrates one protocol for the preparation of 5-(3,3-dichloroprop-2-enyloxy)-1,3-dichloro-2-[5-(2-methylbenzothiazol-5-yloxy)pentyloxy]benzene (Compound 12 in table below)

This compound was prepared in a manner analogous to that of Step D of Example 1, by the reaction of 0.26 gram (0.0006 mole) of 5-(3,3-dichloroprop-2-enyloxy)-2-(5-bromopentyloxy)-1,3-dichlorobenzene (prepared in a manner analogous to Steps C through F of Example 2), 0.1 gram (0.0006 mole) of 2-methyl-5-benzothiazolol (known compound) and 0.17 gram (0.0012 mole) of potassium carbonate in 50 mL of DMF. The reaction product was purified with column chromatography on silica gel using 100% hexane, and finally 25% ethyl acetate in hexane, as eluants. The appropriate fractions were combined and concentrated under reduced pressure, yielding 0.22 gram of Compound 12. The NMR spectrum was consistent with the proposed structure.

EXAMPLE 4

This example illustrates one protocol for the preparation of 5-(3,3-dichloroprop-2-enyloxy)-1,3dichloro-2-{3-[2-(trifluoromethyl)benzoxazol-6-yloxy]propoxy}benzene (Compound 3 in table below)

This compound was prepared in a manner analogous to that of Step D of Example 1, by the reaction of 0.41 gram (0.001 mole) of 1-[4-(3,3-dichloroprop-2-enyloxy)-2,6-dichlorophenoxy]-3-bromopropane (prepared in Steps C through F of Example 2), 0.20 gram (0.001 mole) of 2-(trifluoromethyl)benzoxazol-6-ol (prepared in Steps A through C of Example 1) and 0.12 gram (0.0012 mole) of potassium carbonate in 10 mL of DMF. The reaction product was purified with column chromatography on silica gel using 1:2 hexane:methylene chloride as an eluant. The appropriate fractions were combined and concentrated under reduced pressure, yielding 0.43 gram of Compound 3. The NMR spectrum was consistent with the proposed structure.

The following table sets forth examples of compounds of formula I:

TABLE I

Insecticidal (Dihalopropenyl)phenylalkyl Substituted Benzoxazole and Benzothiazole Derivatives

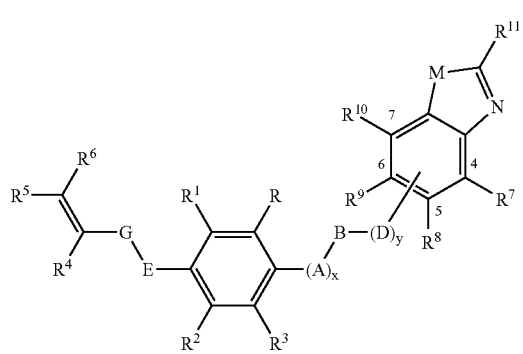

I where B is a bridging group of the formula:
—$(CR^{16}R^{17})_q$—$(CR^{18}R^{19})_r$—$(CR^{20}R^{21})_s$—$L_t$—$(CR^{22}R^{23})_u$—$(CR^{24}R^{25})_v$—$(CR^{26}R^{27})_w$—.
where $R^1$, $R^2$, $R^4$, $R^7$, $R^8$, $R^9$, and $R^{10}$ are hydrogen; R, $R^3$, $R^5$ and $R^6$ are chloro; q, r s, t, u, v and w are 0 or 1, where when q, r s, t, u, v and w are 1, $R^{16}$ through $R^{27}$, inclusively, are hydrogen; x and y are 1; A, D and E are O, and G is $(CH_2)_n$ where n is 1; providing compounds as set forth below:

| Cmpd. No. | Equal to 1 | Equal to 0 | Point of Attchment to Benzo-fused Ring | M | $R^{11}$ |
|---|---|---|---|---|---|
| 1 | q, r, s | t, u, v, w | 5-position | O | $CF_3$ |
| 2 | q, r, s | t, u, v, w | 6-position | O | $CH_3$ |
| 3 | q, r, s | t, u, v, w | 6-position | O | $CF_3$ |
| 4 | q, r, s, u | t, v, w | 5-position | O | $CF_3$ |
| 5 | q, r, s, u | t, v, w | 6-position | O | $CH_3$ |
| 6 | q, r, s, u | t, v, w | 6-position | O | $CF_3$ |
| 7 | q, r, s, u, v | t, w | 5-position | O | $CF_3$ |
| 8 | q, r, s, u, v | t, w | 6-position | O | $CF_3$ |
| 9 | q, r, s | t, u, v, w | 6-position | S | $CH_3$ |
| 10 | q, r, s, u | t, v, w | 5-position | S | $CH_3$ |
| 11 | q, r, s, u | t, v, w | 6-position | S | $CH_3$ |
| 12 | q, r, s, u, v | t, w | 5-position | S | $CH_3$ |
| 13 | q, r, s, u, v | t, w | 6-position | S | $CH_3$ |

The following table sets forth physical characterizing data for certain compounds of formula I of the present invention. The test compounds of formula I are identified by numbers that correspond to those in Table 1:

TABLE 2

Insecticidal (Dihalopropenyl)phenylalkyl Substituted Benzoxazole and Benzothiazole Derivatives; Compound Characterization Characterizing Data

| Cmpd. No. | Emperical Formulae | Physical State | Cmpd. No. | Emperical Formulae | Physical State |
|---|---|---|---|---|---|
| 1 | $C_{20}H_{14}Cl_4F_3NO_4$ | Oil | 2 | $C_{20}H_{17}Cl_4NO_4$ | Oil |
| 3 | $C_{20}H_{14}Cl_4F_3NO_4$ | Colorless Oil | 4 | $C_{21}H_{16}Cl_4F_3NO_4$ | Oil |
| 5 | $C_{21}H_{19}Cl_4NO_4$ | Oil | 6 | $C_{21}H_{16}Cl_4F_3NO_4$ | Liquid/Oil |
| 7 | $C_{22}H_{18}Cl_4F_3NO_4$ | Solid | 8 | $C_{22}H_{18}Cl_4F_3NO_4$ | Colorless Oil |
| 9 | $C_{20}H_{17}Cl4NO3S$ | Oil | 10 | $C_{21}H_{19}Cl_4NO_3S$ | Solid(mp 70–72° C.) |
| 11 | $C_{21}H_{19}Cl_4NO_3S$ | Solid(mp 100–02° C.) | 12 | $C_{22}H_{21}Cl_4NO_3S$ | Solid(mp 57–60° C.) |
| 13 | $C_{22}H_{21}Cl_4NO_3S$ | Oil | | | |

Candidate insecticides were evaluated for activity against the tobacco budworm (*Heliothis virescens [Fabricius]*) in a surface-treated diet test.

In this test one mL of molten (65–70° C.) wheat germ-based artificial diet was pipetted into each well of a four by six (24 well) multi-well plate (ID# 430345-15.5 mm dia.× 17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Certain (Dihalopropenyl)phenylalkyl Substituted Benzoxazole and Benzothiazole Derivatives When Applied to the Surface of the Diet of Tobacco Budworm (*Heliothis virescens* [Fabricius])

| Cmpd. No. | Percent Mortality | Percent Growth Inhibition | Cmpd. No. | Percent Mortality | Percent Growth Inhibition |
|---|---|---|---|---|---|
| 1 | 100 | 100 | 2 | 100 | 100 |
| 3 | 100 | 100 | 4 | 100 | 100 |
| 5 | 100 | 100 | 6 | 100 | 100 |
| 7 | 100 | 100 | 8 | 100 | 100 |
| 9 | 100 | 100 | 10 | 100 | 100 |
| 11 | 100 | 100 | 12 | 100 | 100 |
| 13 | 100 | 100 | | | |

Concentration of the candidate insecticide on the surface of the diet is 0.25 millimolar As set forth in Table 3, all of the compounds of the present invention tested provided 100% mortality and 100% growth inhibition of the tobacco budworm.

Certain compounds of formula I were tested against tobacco budworm on plant foliage. The foliar treated test against tobacco budworm were conducted in the following manner:

Nine-to-ten day-old chick pea plants (*Cicer arietinum*) were sprayed at 15 psi to runoff on both upper and lower leaf surfaces with solutions of test compound to provide application rates as high as 1000 ppm of test chemical. The solvent used to prepare the solutions of test compound was 10% acetone or methanol (v/v) and 0.1% of the surfactant octylphenoxypolyethoxyethanol in distilled water. Four replicates, each containing one chick pea plant, for each rate of application of test compound were sprayed. The treated plants were transferred to a hood where they were kept until the spray had dried.

The four chick pea plants for each replicate treated with test compound as described above were removed from their pots by cutting the stems just above the soil line. The excised leaves and stems from the four plants in each replicate were placed in individual 237 mL (8-ounce) paper cups, which contained a moistened filter paper. Five second-instar tobacco budworm (7 days old) were counted into each cup, taking care not to cause injury. An opaque plastic lid was placed on each cup, which was then held in a growth chamber for a 96 hour exposure period at 25° C. 50% relative humidity and photo-period of 12 hours light and 12 hours dark. At the end of the 96 hour exposure period the cups were opened, and the numbers of dead, moribund, and live insects were counted. Using the insect counts, the efficacy of the test compound was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Larvae are classified as "moribund" if they fail to rapidly right themselves when turned over, but show movement, or if they are severely reduced in size and do not appear to be feeding.

Results of these tests against tobacco budworm are set forth below in Table 4.

TABLE 4

Activity Against Tobacco Budworm on Foliage

| Cmpd. No. | Point of Attchment to Benzo-fused Ring | $R^{11}$ | Percent Control of Tobacco Budworm in a Foliar Test | |
|---|---|---|---|---|
| | | | 30 ppm | 10 ppm |
| 1 | 5-position | $CF_3$ | 95 | 31 |
| 2 | 6-position | $CH_3$ | 25 | 25 |
| 3 | 6-position | $CF_3$ | 100 | 100 |
| 4 | 5-position | $CF_3$ | 55 | 15 |
| 5 | 6-position | $CH_3$ | — | 40 |
| 6 | 6-position | $CF_3$ | 95 | 70 |
| 7 | 5-position | $CF_3$ | 100 | 10 |
| 8 | 6-position | $CF_3$ | 95 | 55 |
| 9 | 6-position | $CH_3$ | — | 10 |
| 10 | 5-position | $CH_3$ | — | 5 |
| 12 | 5-position | $CH_3$ | — | 15 |

As set forth in Table 4, those compounds in which the substituent $R^{11}$ is trifluoromethyl (compounds 1, 3, 4, and 6–8) and methyl (compounds 2, 5, 9, 10 and 12) are active in controlling tobacco budworm. In this test, those compounds where $R^{11}$ is trifluoromethyl are somewhat more active than those compounds where $R^{11}$ is methyl. In addition, those compounds where $R^{11}$ is trifluoromethyl and the benzo-fused ring is attached to the rest of the molecule at the 6-position are somewhat more active than the corresponding compounds where the benzo-fused ring is attached at the 5-position, especially at the lower 10 ppm rate of application.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I:

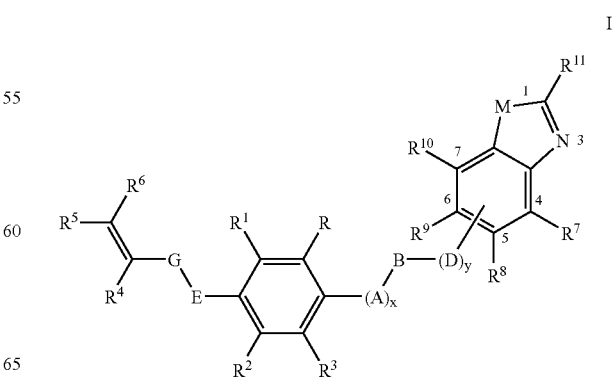

wherein

R and $R^3$ are independently selected from hydrogen, halogen, hydroxy, $(C_1-C_3)$alkyl, $(C_3-C_6)$cycloalkyl, $(C_2-C_5)$alkenyl, $(C_2-C_5)$alkynyl, halo$(C_1-C_3)$alkyl $(C_1-C_3)$alkylsulfonyl, halo$(C_1-C_3)$alkylsulfonyl, cyano, nitro; optionally substituted amino wherein the optional substituent is selected from $(C_1-C_4)$alkyl, $(C_1-C_3)$alkylcarbonyl and $(C_1-C_3)$alkoxycarbonyl; optionally substituted imidazolyl, optionally substituted imidazolinyl, optionally substituted oxazolinyl, optionally substituted oxazolyl, optionally substituted oxadiazolyl, optionally substituted thiazolyl, optionally substituted pyrazolyl, optionally substituted triazolyl, optionally substituted furanyl optionally substituted tetrahydrofuranyl, optionally substituted dioxolanyl, optionally substituted dioxanyl, —C(=J)—K, and —C($R^{12}$)—Q—$R^{13}$, wherein the optional substituent is selected from $(C_1-C_4)$alkyl, halo$(C_1-C_4)$alkyl, $(C_1-C_4)$alkoxy, $(C_{1-4})$alkoxy$(C_1-C_4)$alkyl, $(C_3-C_6)$cycloalkyl, $(C_2-C_5)$alkenyl, $(C_2-C_5)$alkynyl, cyano, nitro and aryl;

where

J is selected from O, S, $NR^{14}$, and $NOR^{14}$, where $R^{14}$ is hydrogen, $(C_1-C_4)$alkyl, halo$(C_1-C_4)$alkyl, aryl and aryl$(C_1-C_4)$alkyl;

K is selected from hydrogen, $(C_1-C_3)$alkyl, halo$(C_1-C_3)$alkyl, $(C_1-C_3)$alkoxy, $(C_1-C_3)$alkylamino and di$(C_1-C_3)$alkylamino;

Q is selected from O, S, and $NR^{14}$, where $R^{14}$ is as previously described;

$R^{12}$ and $R^{13}$ are independently selected from hydrogen, $(C_1-C_4)$alkyl and halo$(C_1-C_4)$alkyl, and $R^{12}$ and $R^{13}$ may be taken together with -T(CH$R^{14}$)$_m$—, where m is an integer of 2 to 4; T is selected from from O, S, and $NR^{14}$, where $R^{14}$ is as previously described;

$R^1$ and $R^2$ are independently selected from hydrogen, halogen and $(C_1-C_3)$alkyl;

$R^4$ is hydrogen;

$R^5$ and $R^6$ are independently selected from halogen;

E is selected from CH$_2$, O, S and $NR^{15}$ where $R^{15}$ is selected from hydrogen, $(C_1-C_3)$alkyl, $(C_1-C_3)$alkoxy $(C_1-C_3)$alkyl, aryl$(C_1-C_3)$alkyl, $(C_2-C_4)$alkenyl $(C_1-C_3)$alkyl, halo$(C_2-C_4)$alkenyl$(C_1-C_3)$alkyl, di$(C_1-C_3)$alkylphosphonate, formyl, $(C_1-C_3)$alkylcarbonyl, halo$(C_1-C_3)$alkylcarbonyl, $(C_1-C_3)$alkoxy $(C_1-C_3)$alkylcarbonyl, arylcarbonyl and $(C_1-C_3)$alkylsulfonyl;

G is selected from O, S, CH$_2$O* and (CH$_2$)$_n$ where the asterisk denotes attachment to E, and n is an integer selected from 1, 2 and 3, provided that E and G are not simultaneously O or S, x is an integer selected from 0 or 1;

and when x is 1,

A is selected from O, S(O)$_p$ and —$NR^{15}$, where p is an integer selected from 0, 1 and 2, and $R^{15}$ is as previously described;

B is a bridging group, *—(C$R^{16}R^{17}$)$_q$—(C$R^{18}R^{19}$)$_r$—(C$R^{20}R^{21}$)$_s$—L$_t$—(C$R^{22}R^{23}$)$_u$—(C$R^{24}R^{25}$)$_v$—(C$R^{26}R^{27}$)$_w$—, where the asterisk denotes attachment at A; q, r, s, u, v and w are integers independently selected from 0, 1 and 2; and when q, r, s, u, v or w are 1 or 2, $R^{16}$ through $R^{27}$, inclusively, are independently selected from hydrogen, $(C_1-C_3)$alkyl, halo$(C_1-C_3)$alkyl, $(C_1-C_3)$ alkoxy$(C_1-C_3)$alkyl, and $(C_3-C_6)$cycloalky;

t is an integer selected from 0 or 1; and when t is 1,

L is selected from CH=CH; O, S(O)$_p$; OS(O)$_z$, S(O)$_2$O, $NR^{28}$; N(oxide)$R^{28}$; $NR^{28}SO_2$; $NR^{28}$C(=O)$NR^{29}$; Si(CH$_3$)$_2$; C(=O), OC(=O), NHC(=O); ON=CH; HC=NO; C(=O)O; C(=O)NH; C(=$NOR^{14}$) and [C$R^{30}R^{31}$]$_z$, where p is as previously described, $R^{28}$ and $R^{29}$ are independently selected from hydrogen, $(C_{1-3})$alkyl, $(C_{1-3})$alkylsulfonyl, $(C_{1-3})$alkylcarbonyl, $(C_2-C_5)$alkenyl, and $(C_2-C_5)$alkynyl; z is an integer selected from 1 or 2; and $R^{30}$ and $R^{31}$ are independently selected from hydrogen and $(C_1-C_3)$alkyl;

y is an integer selected from 0 or 1;

and when y is 1,

D is selected from O; S(O)$_p$; and $NR^{15}$, where p and $R^{15}$ are as previously described, wherein D is attached to the benzo-fused ring moiety set forth in formula I at any one of the positions designated 4-, 5-, 6- or 7-:

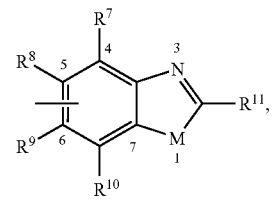

$R^7$, $R^8$, $R^9$ and $R^{10}$ are independently selected from hydrogen, halogen, $(C_1-C_4)$alkyl, $(C_3-C_6)$cycloalkyl, $(C_2-C_5)$alkenyl, $(C_2-C_5)$alkynyl, halo$(C_1-C_4)$alkyl $(C_1-C_4)$alkoxy, halo$(C_1-C_4)$alkoxy, $(C_1-C_4)$alkylthio, halo$(C_1-C_4)$alkylthio, $(C_1-C_4)$alkylsulfonyl, halo$(C_1-C_4)$alkylsulfonyl, cyano, nitro, aryl, alkylcarbonylamino, arylcarbonylamino, and $(C_1-C_4)$alkoxycarbonylamino;

$R^{11}$ is selected from hydrogen, halogen, hydroxyl, cyano, $(C_1-C_6)$alkyl, $(C_1-C_6)$alkoxy, halo$(C_{1-6})$alkyl, halo$(C_{1-6})$alkoxy, $(C_{2-6})$alkenyl, $(C_2-C_6)$alkynyl, $(C_1-C_6)$cycloalkyl, amino, $(C_1-C_6)$alkylamino, di$(C_1-C_6)$alkylamino, $(C_1-C_6)$alkylthio, aryl, arylthio, tri$(C_1-C_6)$alkylsilyl, SF$_5$, C(=O)$NR^{14}$ and $NOR^{14}$ where $R^{14}$ is as previously described;

M is O or S;

and agriculturally acceptable salts thereof.

2. A compound of claim 1, wherein R and $R^3$ are independently selected from halogen and $(C_1-C_3)$alkyl;

$R^1$, $R^2$, and $R^4$ are hydrogen;

$R^5$ and $R^6$ are independently selected from chlorine, bromine, and fluorine;

E is O;

G is (CH$_2$)$_n$, where n is 1;

x is 1, and A is O;

and when q, r, s, u, v and w are 1 or 2, $R^{16}$ through $R^{27}$, inclusively, are hydrogen;

t is 0 or 1, and when t is 1,

L is selected from O, OC(=O), NHC(=O), ON=CH, and CH=NO;

y is 1, and

D is selected from O; S(O)$_p$; and $NR^{15}$, where p is 0, and $R^{15}$ is selected from hydrogen, $(C_1-C_3)$alkyl, aryl $(C_1-C_3)$alkyl, $(C_2-C_4)$alkenyl$(C_1-C_3)$alkyl, and halo ($C_2$–$C_4$)alkenyl($C_1$–$C_3$)alkyl, wherein D is attached to the benzo-fused moiety set forth in formula I at the position designated 5 or 6;

$R^7$, $R^8$, $R^9$ and $R^{10}$ are independently selected from hydrogen, halogen, halo($C_1$–$C_4$)alkyl and nitro; and $R^{11}$ is selected from ($C_1$–$C_4$)alkyl and halo($C_1$–$C_4$)alkyl.

3. A compound of claim 2, wherein R and $R^3$ are independently selected from chlorine and methyl;

$R^5$ and $R^6$ are independently selected from chlorine and bromine;

q, r, s, u, v and w are 1 or 2, provided that the sum of q, r, s, u, v and w is at least 2 and at most 6;

t is 0;

D is O, wherein D is attached to the benzo-fused moiety set forth in formula I at the position designated as 5 or 6;

$R^7$, $R^8$, $R^9$ and $R^{10}$ are hydrogen; and $R^{11}$ is methyl or trifluoromethyl.

4. A compound of claim 3, wherein R, $R^3$, $R^5$ and $R^6$ are each chlorine; q, r and s are 1; u and v are 0 or 1; w is 0; M is O and $R^{11}$ is trifluoromethyl.

5. A compound of claim 3, wherein R, $R^3$, $R^5$ and $R^6$ are each chlorine; q, r and s are 1; u and v are 0 or 1; w is 0; M is S and $R^{11}$ is methyl.

6. A composition comprising an insecticidally effective amount of a compound of claim 1 in admixture with at least one agriculturally acceptable extender or adjuvant.

7. The insecticidal composition of claim 6, further comprising one or more second compounds selected from the group consisting of pesticides, plant growth regulators, fertilizers and soil conditioners.

8. A method of controlling insects, comprising applying an insecticidally effective amount of a composition of claim 6 to a locus where insects are present or are expected to be present.

9. A method of controlling insects, comprising applying an insecticidally effective amount of a composition of claim 7 to a locus where insects are present or are expected to be present.

10. A compound of formula I:

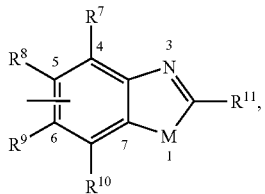

wherein

R and $R^3$ are independently selected from hydrogen, halogen or ($C_1$–$C_3$)alkyl;

$R^1$ and $R^2$ are hydrogen;

E is O; G is $(CH_2)_n$ where n is 1;

$R^4$ is hydrogen;

$R^5$ and $R^6$ are independently selected from halogen;

x is 1 and A is O;

B is a bridging group *—$(CR^{16}R^{17})_q$—$(CR^{18}R^{19})_r$—$(CR^{20}R^{21})_s$—$L_t$—$(CR^{22}R^{23})_u$—$(CR^{24}R^{25})_v$—$(CR^{26}R^{27})_w$—, where the asterisk denotes attachment at A; q, r, s, u, v and w are integers independently selected from 0, 1 and 2; and t is 0;

and when q, r, s, u, v or w are 1 or 2, $R^{16}$ through $R^{27}$, inclusively, are hydrogen, y is 1, and D is O, and wherein D is attached to the benzo-fused ring moiety set forth in formula I at either one of the positions designated 5- or 6-:

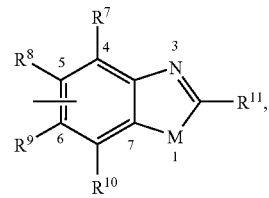

$R^7$, $R^8$, $R^9$ and $R^{10}$ are independently selected from hydrogen, halogen or ($C_1$–$C_4$)alkyl;

$R^{11}$ is selected from ($C_1$–$C_3$)alkyl and halo($C_1$–$C_3$)alkyl; and

M is O or S.

11. A compound of claim 10, wherein R and $R^3$ are independently selected from chlorine and methyl;

$R^5$ and $R^6$ are independently selected from chlorine and bromine;

q, r, s, u, v and w are 0, 1 or 2, provided that the sum of q, r, s, u, v and w is at least 2 and at most 6;

$R^7$, $R^8$, $R^9$ and $R^{10}$ are hydrogen; and $R^{11}$ is methyl or trifluoromethyl.

12. A compound of claim 11, wherein R, $R^3$, $R^5$ and $R^6$ are each chlorine; q, r and s are 1; u and v are 0 or 1; w is 0; M is O and $R^{11}$ is trifluoromethyl.

13. A compound of claim 11, wherein $R^3$, $R^5$, and $R^6$ are each chlorine; q, r and s are 1; im amd v are 0 or 1; w is 0; M is S and $R^{11}$ is methyl.

* * * * *